United States Patent [19]

Hayashi et al.

[11] 4,404,682
[45] Sep. 13, 1983

[54] METHOD FOR FORESEEING RESIDUAL LIFE OF STRUCTURAL MEMBER MAKING USE OF X-RAY

[75] Inventors: Makoto Hayashi; Tasuku Shimizu, both of Hitachi, Japan

[73] Assignee: Hitachi, Ltd., Tokyo, Japan

[21] Appl. No.: 217,083

[22] Filed: Dec. 16, 1980

[30] Foreign Application Priority Data

Dec. 19, 1979 [JP] Japan .................. 54/165246

[51] Int. Cl.³ ........................................... G01N 23/20
[52] U.S. Cl. .................................................. 378/72
[58] Field of Search ................. 378/71, 72; 73/577, 73/808, 810

[56] References Cited

U.S. PATENT DOCUMENTS 3,228,238 1/1966 Jentet .................................. 73/577
3,631,713 1/1972 Marom et al. ...................... 73/577
3,934,138 1/1976 Bens ................................... 378/72

FOREIGN PATENT DOCUMENTS

2742478 3/1979 Fed. Rep. of Germany.

*Primary Examiner*—Bruce C. Anderson
*Assistant Examiner*—Jack I. Berman
*Attorney, Agent, or Firm*—Thomas E. Beall, Jr.

[57] ABSTRACT

Provided is a method for foreseeing the residual life of a structural member, making use of an X-ray, comprising: preparing a plurality of test pieces made of the same material and subjected to the same working and heat-treating conditions as the structural member to be examined of which the fatigue strength is in question; executing fatigue tests with said test pieces till failure under a plurality of different stress conditions; obtaining for each stress the relationship between the residual life of said test piece and the halfvalue width ratio of X-ray diffraction profile; determining, from the above-mentioned relationships, a first relationship region between the halfvalue width ratio and the residual life that is independent of the level of the stress; measuring the halfvalue width ratio of said structural member; and determining the residual life of said structural member from the measured halfvalue width ratio in accordance with said first relationship region.

6 Claims, 11 Drawing Figures

METHOD FOR FORESEEING RESIDUAL LIFE OF STRUCTURAL MEMBER MAKING USE OF X-RAY

BACKGROUND OF THE INVENTION

The present invention relates to a method of determining the residual life of mechanical structures, especially those of which the fatigue strength is in question, making use of X-ray.

Generally, the structural members constituting a mechanical structure are designed to be subjected to stresses of levels below the fatigue limit of the material. In the actual use, however, the structural member is often subjected to stresses of levels higher than the designed stress for various reasons, and is failed due to such stresses. In order to prevent such a failure, it is necessary to determine the residual life of the structural member being used.

Various methods have been proposed hitherto for determining the residual life of the structural member. For instance, according to one known method a metal foil is adhered to the structural member of which the fatigue strength is in question, or a test piece having a plurality of notches with more than two different stress concentration coefficients is attached to the structural member. Then, after the fatigue, the X-ray diffraction intensity is measured with the metal foil or the test piece. The residual life of the material or the extent of damage is then detected through the calculation of the integrated value of the X-ray diffraction intensity profile or from the amount of change in the halfvalue width. This conventional method, however, necessitates the attaching of the metal foil or the test piece to the structural member to be examined.

Further, in most cases it is not possible to attach the metal foil or test piece to the structural member under the use. Even when the attachment is possible, the method relying upon the adhesion of the metal foil cannot detect the damage due to fatigue caused by compression stress.

Under this circumstance, the present applicant has proposed in Japanese Patent Application Laid-open Publication No. 20894/76 a new method comprising the steps of determining the relationship between the stress amplitude and the stress number till rupture, from the rate of change in residual stress obtained through an X-ray diffraction, detecting the ratio of the amount of change in residual stress to the initial residual stress through measurement of position by the X-ray diffraction profile, and calculating the number of repetition of stresses till failure. This method, however, necessitates the determination of ratio of amount of change in the residual stress to the initial residual stress, which in turn requires a stress measurement by X-ray. It is quite troublesome and difficult to conduct this measurement.

In another known method for determining the residual life, a strain guage is adhered to the surface of the structural member of which the fatigue strength is in question to measure the stress in the structural member. The measured stress values are compared with the values in a S-N curve (a curve of stress vs. number of repetitions of stress) which is previously drawn through experimental fatigue tests carried out in a laboratory, and the limit of use, i.e. the residual life, is determined by reading the number of repetition of stress from the S-N curved. As a matter of fact, however, the structural member often makes a motion such as rotation. In such a case, it is not possible to adhere the strain gauge to the structural member to be examined.

The X-ray diffraction method, therefore, has been proposed as a method which makes it possible to measure the degree of damage due to fatigue without direct measurement of the stress.

Briefly, this method is to make use of such a phenomenon that the halfvalue width of an X-ray diffraction intensity profile obtained by irradiating an X-ray to the object varies depending on the distortion attributable to fatigue. Namely, the degree of damage is detected as the ratio of the halfvalue width before the fatigue to the halfvalue with after the fatigue.

Hitherto, when a damage is found out in a structural member, the latter is replaced with a new member without delay, because the damage is expected to develop to cause a failure sooner or later. It takes a considerably long period of time for the renewal of the structural member. Also, the fabrication of new structural member incurs a rise of cost.

In contrast, it is a current measure to determine the residual life of the structural member, from the detection of degree of the damage, and to use the member almost to the expiration of the life thereby to reduce the cost incurred. The determination of the residual life can be made by a conventional method using X-ray but this known method involves various problems. More specifically, this method is to determine the stress applied to the member from the halfvalue width ratio and, using the stress thus obtained, the number of repetition of stress till rupture from an S-N curve. Then, the residual life is calculated by subtracting the number of repetition of stress till the measurement of the halfvalue width from the number of repetition of stress till failure. Alternatively, by making use of a fact that the halfvalue width ratio corresponds in certain extent to the number of repetition of the stress, the residual life is determined from the halfvalue width ratio and the number of repetition of stress. As a matter of fact, however, there are only few cases that the record of change in stress in a structural member is available. Therefore, it has been almost impossible to know the residual life by the known methods.

OBJECTS OF THE INVENTION

It is, therefore, a first object of the invention to provide a simple method easy to carry out for determining the residual life of a structural member making use of an X-ray.

It is a second object of the invention to provide a simple method easy to carry out for determining the residual life of a structural member, making use of an X-ray, which is applicable to a large size structural member when a crack has been initiated therein.

SUMMARY OF THE INVENTION

To this end, according to an aspect of the invention, there is provided a method for determining the residual life of a structural member, making use of an X-ray, comprising: preparing a plurality of test pieces made of the same material and subjected to the same working and heat-treating conditions as the structural member to be examined of which the fatigue strength is in question; executing fatigue tests with said test pieces till failure under a plurality of different stress conditions; obtaining for each stress the relationship between the residual life of said test piece and the halfvalue width ratio of the X-ray diffraction profile; determining, from the above-mentioned relationships, a first relationship between the residual life and the halfvalue width ratio, said first relationship being independent of the level of the stress; measuring said halfvalue width ratio of said structural member; and determining the residual life of said structural member from the measured halfvalue width ratio in accordance with said first relationship.

According to another aspect of the invention, there is provided a method of determining the residual life of a structural member in which a crack has been initiated, making use of an X-ray, comprising the steps of determining a second relationship between the crack length and the residual life from the relationship between the halfvalue width ratio and the crack growth (or development) rate, and determining the residual life of the structural member from the measured crack length in the actual structural member in accordance with the above-mentioned second relationship.

DESCRIPTION OF THE PREFERRED EMBODIMENTS

The invention will be described hereinunder with reference to the accompanying drawings.

Figure 1:
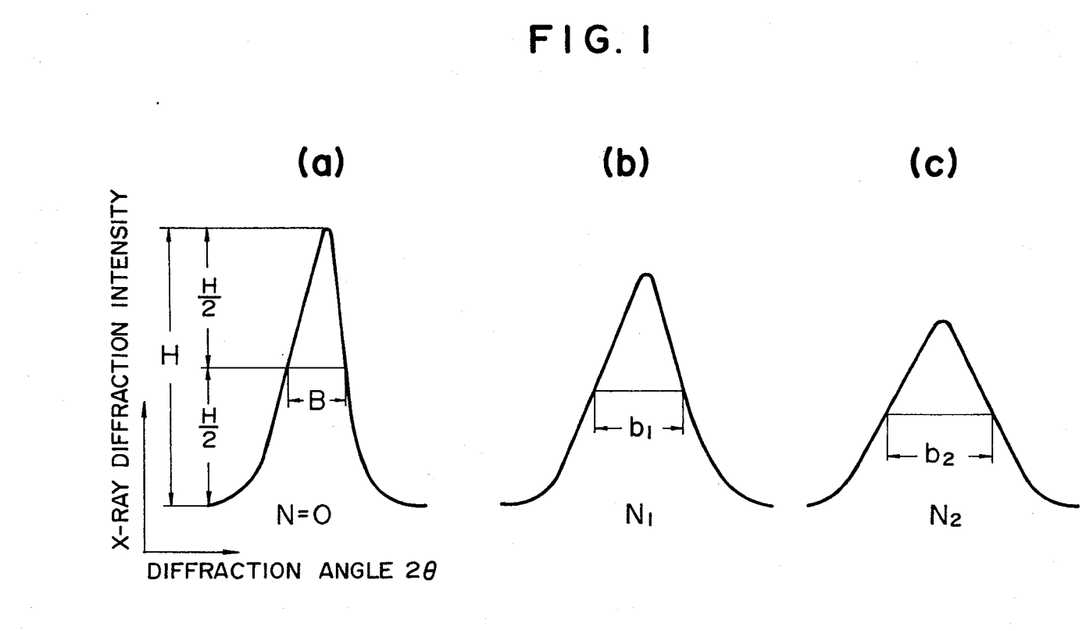
FIG. 1 is a graph showing X-ray diffraction intensity profiles as observed before and after a fatigue.
Figure 2:
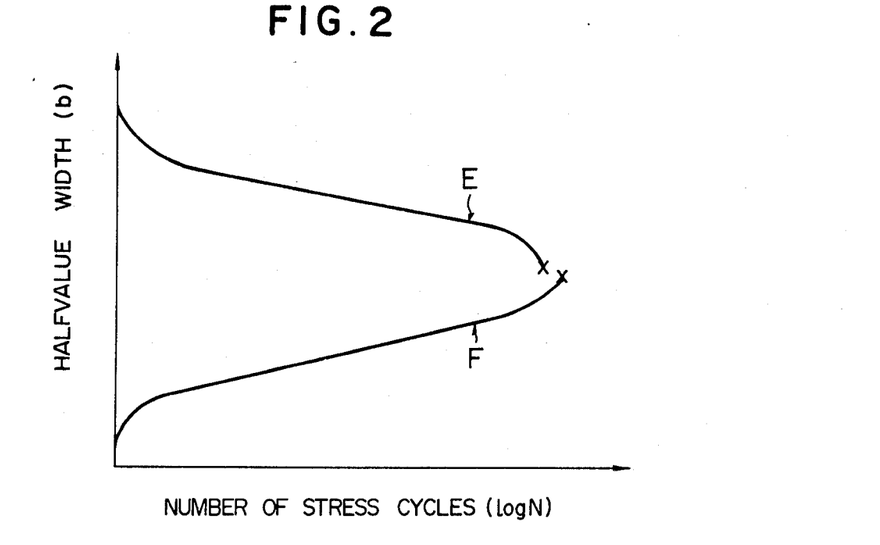
FIG. 2 is a graph showing the relationship between the number of repetition of stress and the halfvalue width in each of an annealed material and a worked material.

The present invention is based upon the following theory. FIGS. 1a, 1b and 1c show, by way of example, X-ray diffraction intensity profiles drawn on an annealed material in the fatigue process. In each Figure, the axis of abscissa and axis of ordinate represent, respectively, the diffraction angle $2\theta$ and the X-ray diffraction intensity. More specifically, FIGS. 1a, 1b and 1c show the characteristics when the number N of repetition of stress is 0 (zero), $N_1$ and $N_2$ ($N_1 < N_2$). A symbol H represents the height of the X-ray diffraction intensity profile, while B, $b_1$ and $b_2$ represent, respectively, halfvalue width in respective curves. As will be clearly seen from these Figures, there is a relation expressed by $B < b_1 < b_2$. Namely, the halfvalue width is increased as the number of repetition of stress is increased. On the other hand, in the worked material, the halfvalue width is greater than that of the annealed material due to the plastic deformation and, contrarily to the case of the annealed material, the halfvalue width is gradually decreased as the fatigue damage grows with the increase in the number of repetition of the stress. These relationships are shown in FIG. 2, in which symbols E and F represent, respectively, a worked material and an annealed material.

Figure 3:
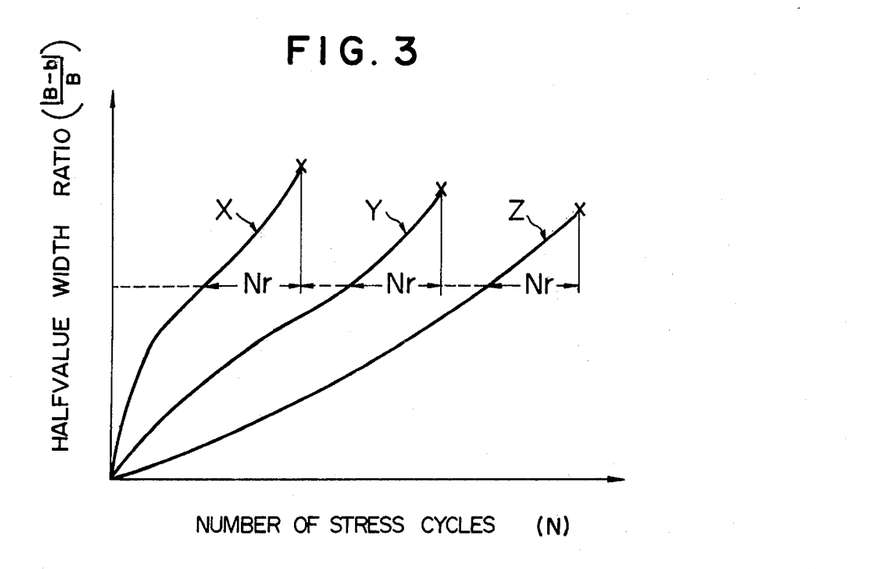
FIG. 3 is a graph showing the change of the halfvalue width ratio in the fatigue process.

FIG. 3 shows the change in the halfvalue width ratio due to the repetition of stress. In this Figure, axis of abscissa and axis of ordinate represent, respectively, the number N of repetition of stress and the halfvalue width ratio $|B-b|/B$. Symbols X, Y and Z correspond to stress amplitudes $\sigma_1$, $\sigma_2$ and $\sigma_3$ ($\sigma_1 > \sigma_2 > \sigma_3$). The points of failure are marked at x. Also, the residual life is represented by Nr. This chart shows that the change of the halfvalue width ratio $|B-b|/B$ becomes great as the stress amplitude is increased.

Figure 4:
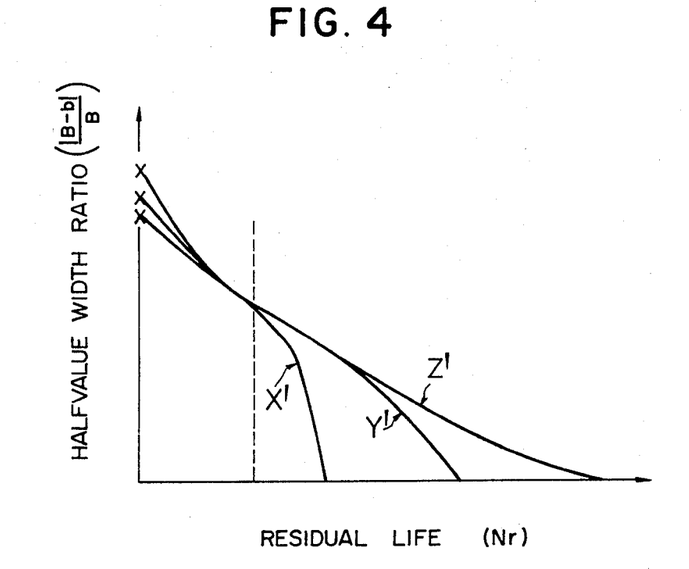
FIG. 4 is a graph showing the relationship between the halfvalue width ratio $|B-b|/B$ and the residual life as obtained from the characteristic shown in FIG. 3.

FIG. 4 shows the relationship between the residual life and the halfvalue width ratio as derived from the curves shown in FIG. 3. More specifically, in FIG. 4, the axis of abscissa and the axis of ordinate represent, respectively, the residual life Nr and the halfvalue width ratio $|B-b|/B$. Curves X', Y' and Z' represent, respectively, the relationships as obtained when the amplitudes of stress are $\sigma_1$, $\sigma_2$ and $\sigma_3$. From FIG. 4, it will be seen that an interval of the values of the halfvalue width ratio $|B-b|/B$ are concentrated approximately on a common curve in the region of short residual life (left side of the vertical broken line of Figure), i.e. after application of a certain number of stresses. This means that, independently of applied stress, the residual life can be determined through the measurement of the halfvalue width ratio $|B-b|/B$ when within the range of ratios corresponding to this common curve.

The relationship mentioned above between the residual life and the halfvalue width ratio $|B-b|/B$ can be represented graphically by a curve, the common curve B. This curve, which is used as a reference or master when obtaining the residual life, will be referred simply as "master curve", hereinafter.

Thus, the objects of the invention are achieved by determining the master curve showing the relationship between the residual life and halfvalue width ratio $|B-b|/B$ wherein such relationship is substantially independent of applied stress.

Further, in case that the structural member to be examined has a large size, the relationship between the crack length and the residual life is beforehand determined from the relationship between the halfvalue width ratio and the crack growth rate, so that the residual life is determined from the thus determined relationship through measurement of the crack length.

DESCRIPTION OF THE PREFERRED EMBODIMENTS

The invention will be described hereinunder with reference to the accompanying drawings.

Figure 5:
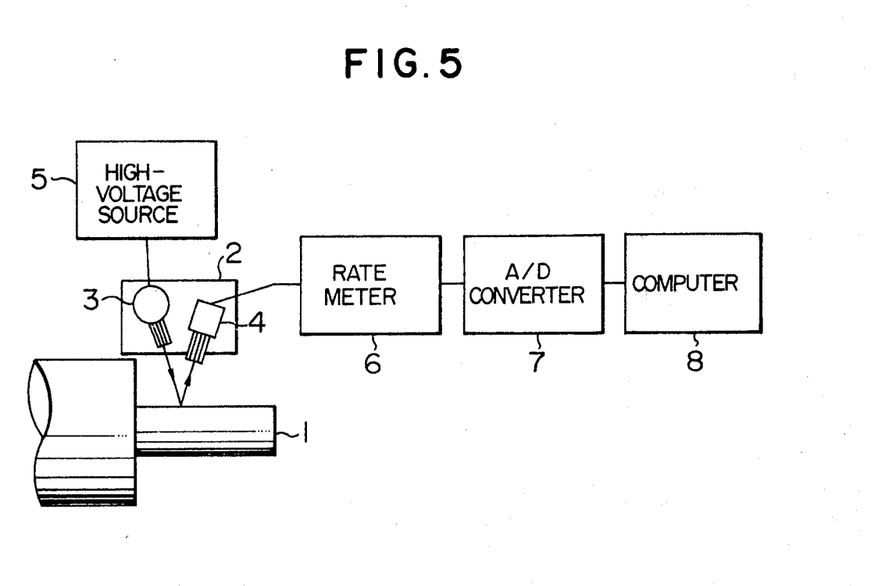
FIG. 5 is a block diagram of an X-ray diffraction device suitable for use in determining the residual life in accordance with a method of the invention making use of an X-ray.

Referring to FIG. 5 showing an X-ray diffraction device suitable for use in carrying out the method of the invention for determining the residual life, a reference numeral 1 denotes a structural member to be examined, 2 denotes an X-ray stress measuring device incorporating an X-ray source 3 and a detector 4, 5 denotes a high-voltage source for generating the X-ray, 6 denotes a rate meter, 7 denotes an A/D converter, and 8 denotes a computer.

For determining the residual life with this device, an X-ray coming from the X-ray source 3 is irradiated to the member 1 to be examined, and the diffracted X-ray from the member 1 is detected by the detector 4. The detected X-ray is then converted into an analog signal by the rate meter 6 and an X-ray diffraction intensity/$2\theta$ profile is obtained with this analog signal. The signal is then input to the computer 8 through the A/D converter 7. Thus, by storing the previously determined master curve in the computer 8, it is possible to determine the residual life through a comparison of the input to the computer 8 from the A/D converter 7 with the master curve.

Figure 6:
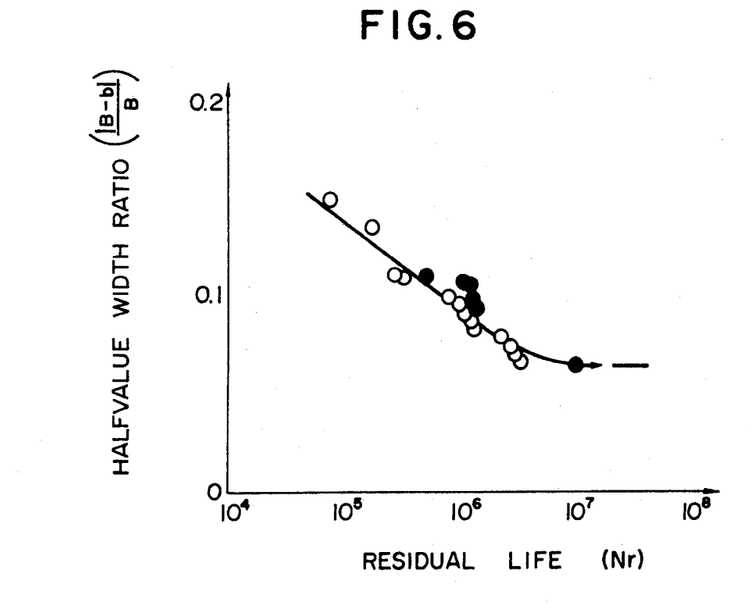
FIGS. 6 and 7 show graphs which are used as master curves in different embodiments of the invention.
Figure 7:
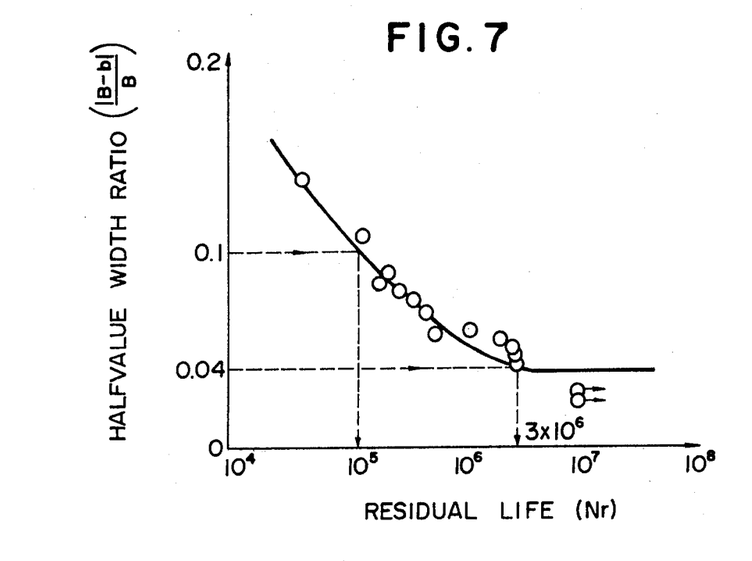

FIGS. 6 and 7 show different examples of the master curve. More specifically, FIG. 6 shows a master curve drawn for an annealed material carbon steel (SFA 55), while FIG. 7 shows the master curve drawn for a turned material (SFA 55). The axis of abscissa and axis of ordinate represent, respectively, the residual life Nr and the halfvalue width ratio $|B-b|/B$. Solid or black circles and blank or white circles show the values obtained with the materials of 10 mm dia. and 20 mm dia., respectively. Thus, different master curves are drawn for materials which have undergone different working and heat-treating conditions. For determing the residual life, the master curve is determined before-hand for each material, and the member to be examined is set in the device shown in FIG. 5 for the measurement of the halfvalue width of this member. Then, the measured data are delivered to a computer in which the program has been formed beforehand to compare the measured halfvalue width with the master curve for the member to be examined. The computer then produces an output representing the residual life, upon comparison with the master curve shown, for example, in FIG. 6 or FIG. 7. For instance, assuming here that the tested member is a mechanical part made of SFA 55 material and worked by turning, it is seen from the curve shown in FIG. 7 that the residual life is about $10^5$ cycles and $3 \times 10^6$ cycles, respectively, when the halfvalue width ratio is measured to be 0.1 and 0.04.

Since the master curve differs depending on the kind of the material, condition of heat-treatment and the condition of the mechanical working, it is necessary to determine the master curve for each material and each condition. However, once the master curve is drawn, it can conveniently be used repeatedly. In addition, the troublesome work of adhering the metal foil or attaching the test piece to the member to be examined, which has been necessary at each time of measurement in a conventional method, is completely avoided.

Figure 8:
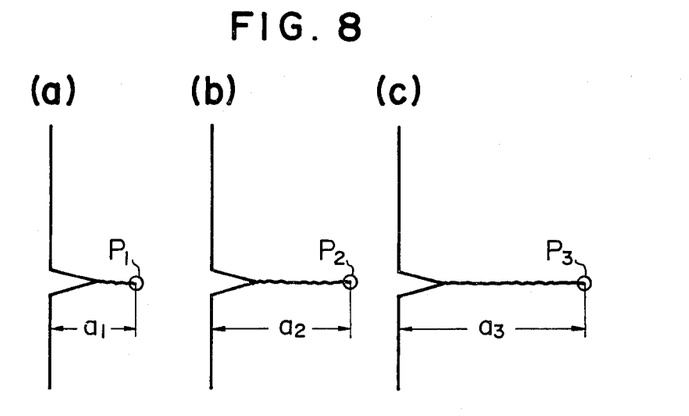
FIG. 8 is a schematic illustration showing the process of the determination of the master curve for a cracked material.
Figure 9:
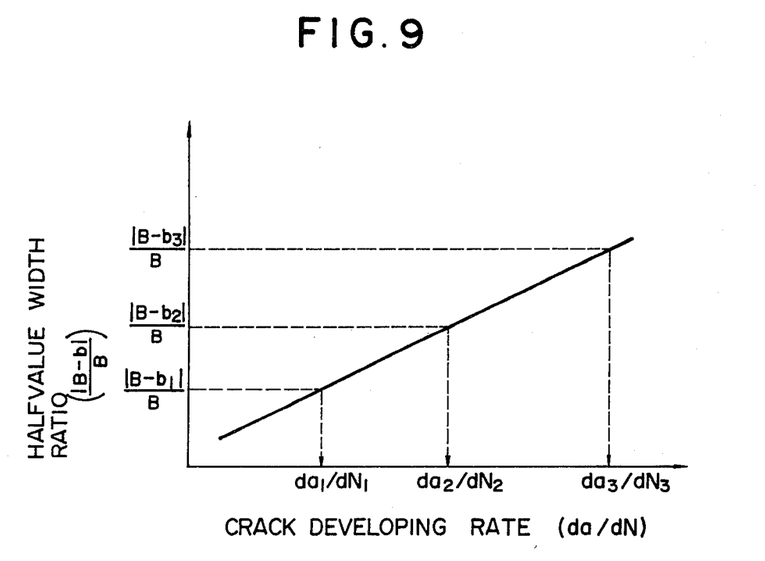
FIG. 9 is a graph explaining the process for determining the crack growth rate.

In case of a cracked material, an X-ray focussed by a pinhole slit is irradiated to each minute region $P_1$, $P_2$ and $P_3$ at the crack tips, as shown in FIGS. 8a, 8b and 8c, and the diffraction X-ray profile is obtained for each case. There is a relationship, as shown in FIG. 9, between the halfvalue width ratio $|B-b|/B$ and the crack growth rate da/dN. The symbol a is used here to represent the distance between the surface and the crack tip, which is referred to as "crack length". Thus, $a_1$, $a_2$ and $a_3$ correspond, respectively, to the cases of FIGS. 8a, 8b and 8c. In FIG. 9, the axis of abscissa and axis of ordinate represent, respectively, the crack growth rate da/dN and the halfvalue width ratio $|B-b|/B$.

It is confirmed that a relation given by the following equation (1) exists over a wide range of da/dN:

$$da/dN = m\left(\frac{|B-b|}{B}\right)^n \quad (1)$$

where, m and n are constants.

Therefore, by measuring the halfvalue width $b_i$ at a given number N of repetition of stress at the crack tip, it is possible to determine the crack growth rate $(da/dN)_i$ from the relationship shown in FIG. 9.

Thus, a crack growth curve can be obtained by measuring the halfvalue width at the crack tips for several times with a certain interval of stress repetition number.

Figure 10:
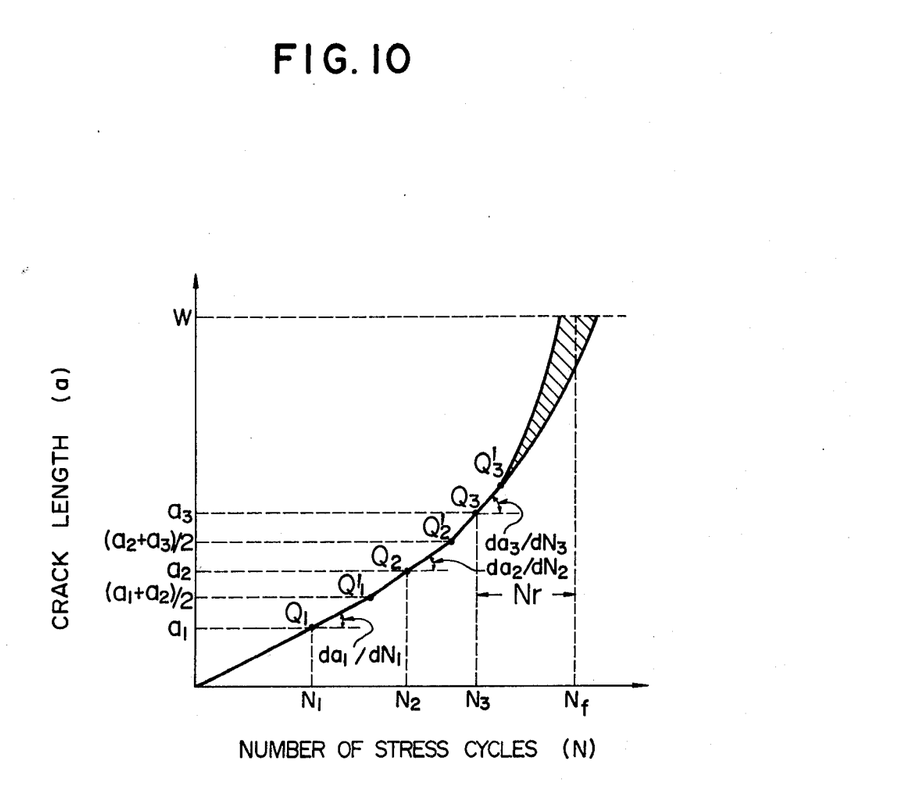
FIG. 10 is a graph explaining the process for obtaining the crack development curve as the master curve for a cracked material.

FIG. 10 illustrates how the crack growth curve is obtained. By measuring the halfvalue widths $b_1$, $b_2$ and $b_3$, it is possible to know respective rates $da_1/dN_1$, $da_2/dN_2$ and $da_3/dN_3$ at respective instants from FIG. 9.

Referring now to FIG. 10, the axis of ordinate represents the crack length a, while the axis of abscissa represents the number N of repetition of the stress. A straight line of a gradient $da_1/dN_1$ is drawn from the point $Q_1$ of intersection between the crack length $a_1$ and the number $N_1$ of repetition of stress to the point of origin 0. This straight line is extended to a point $Q_1'$ where it intersects a broken line which represents $(a_1+a_2)/2$. Then, a straight line of a gradient $da_2/dN_2$ is drawn from a point $Q_2$ at which the line of crack length $a_2$ intersects the line $N_2$ of stress repetition number to the aforementioned point $Q_1'$. This line is extended to a point $Q_2'$ where it intersects a broken line representing $(a_2+a_3)/2$. It is possible to obtain the crack growth curve by repeating this procedure. Since an exponential relationship exists between the crack length a and the number N of repetition of stress that is expressed by the equation (1), it is possible to determine the crack growth after the development of crack to the crack length $a_3$, so that the number $N_f$ of repetition of cycle till the crack growth to the limit or maximum crack length W can be determined. It is, therefore, possible to know the residual life Nr from the crack length a.

Figure 11:
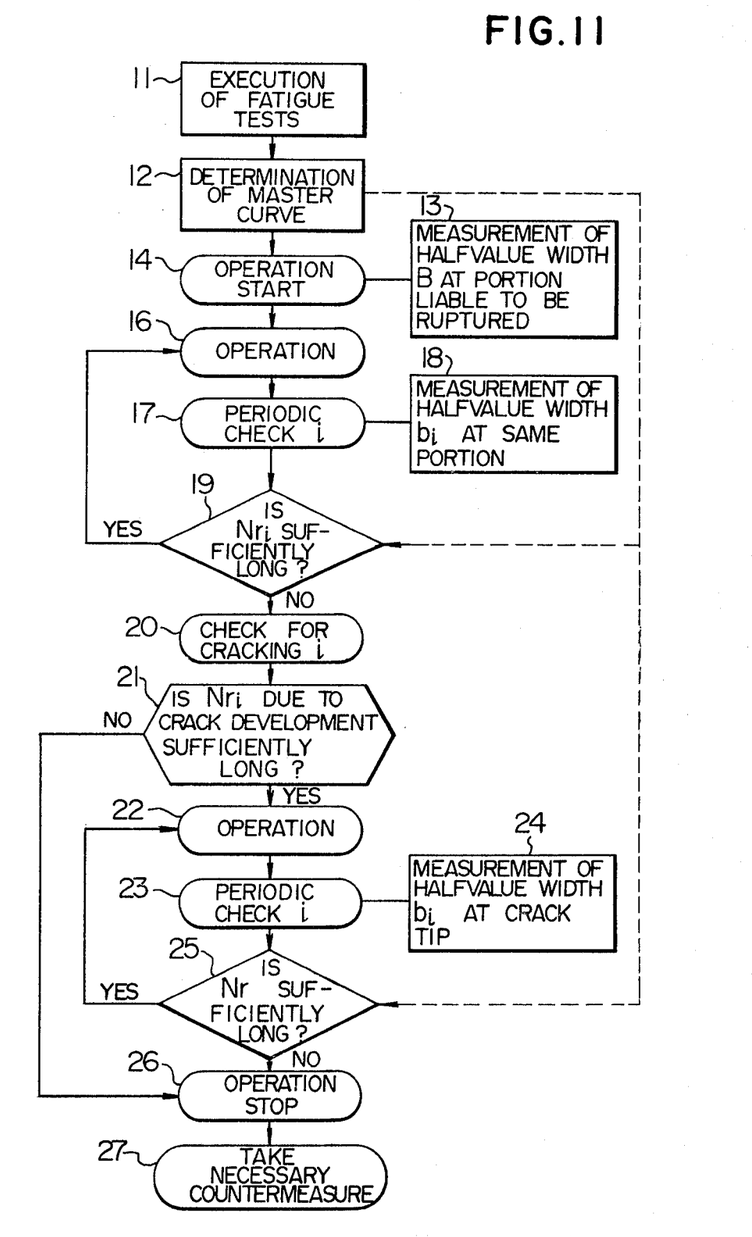
FIG. 11 is a flow chart of an example of the method of the invention for determining the residual life of a structural member, making use of an X-ray.

FIG. 11 is a flow chart of a process for determine the residual life of an actual structural member. First of all, flat test pieces and notched test pieces are fabricated from the same material as the objective structural member, under the same heat-treating condition and woring condition, and fatigue tests are executed (step 11) with these test pieces to draft master curves as shown in FIGS. 6, 7 or 10 (step 12). Then, the initial halfvalue width B is measured at the portion of the structural member liable to be failed (step 13). Then, the machine incorporating the structural member starts to operate (step 14) and the operation is continued (step 16). At each of several successive periodic checks i (17), the halfvalue width $b_i$ is measured (step 18) and the residual life is obtained from the master curve. In the event that the number of repetition of stress at the time of the periodic check is unknown, the residual life can be determined by measuring the halfvalue width and substituting the thus measured half-value width to the master curve showing the relation between the halfvalue width ratio $|B-b|/B$ and the residual life Nr as obtained through experiments, e.g. for the $b_i$ of FIG. 6. Then, a judgement is made as to whether the residual life thus determined is sufficiently long (step 19). The machine incorporating the structural member is started if the residual life $Nr_i$ is sufficiently long to permit a further operation of the machine without renewal of the structural member. However, in case that the residual life $Nr_j$ is not sufficiently long, i.e. that the residual life is considerably short, the use of the structural member is stopped and the structural member is renewed or repaired.

This process is applied to determine the residual life in so-called small articles.

In the event that the structural member to be examined is a so-called large article, the check of crack length is made (step 20) to determine if the residual life $Nr_j$ is not sufficiently long. In the event that a crack is found out and judgement is made that a considerably large number of repetition of stress is required for the development of the crack, the halfvalue width at the crack tip is measured several times at suitable time intervals as shown in FIG. 8. Then, the residual life is determined upon comparison with the master curve shown in FIG. 10, from the relationship shown in FIG. 9 between the halfvalue width ratio $|B-b|/B$ and the crack growth rate $da/dN$. Then, the judgement is made as to whether the residual life $Nr_j$ is sufficiently long (step 21). If it is judged that the residual life is not sufficiently long, the machine is stopped (step 26) and a suitable countermeasure is taken (step 27). The operation of the machine is continued (step 22) if it is judged that the residual life $Nr_j$ is suffuciently long. When the operation of the machine is continued, it is necessary to make the measurement (step 24) of the halfvalue width $b_i$ at the crack tip at each of successive periodic checks (step 23) and to make a judgement as to whether the residual life $Nr_j$ is sufficiently long (step 25).

In case that the material of the structural member is a carbon steel, there is a distinctive fatigue limit. A relationship similar to that of a S-N curve (stress-number of repetition of stress) exists also between the change of the halfvalue width and the residual life. It is considered that, as shown in FIG. 6 in case of the annealed material, the amplitude of stress applied to the material is considered to be lower than the fatigue limit, when the change of the halfvalue width is 0.07 or smaller (corresponds to halfvalue width ratio of 1.07 or smaller), so that the residual life is sufficiently long and there is no fear of breakdown. The same applies to the structural member worked by turning, when the change of the halfvalue width is 0.04 or smaller (corresponds to halfvalue width ratio of 0.96 or greater) as shown in FIG. 7.

Steel materials have distinctive fatigue limits and no failure will occur so long as the level of the stress applied is below the fatigue limit. In S-N curves, the flexure point which corresponds to the fatigue limit appears at about $10^6$ cycles in the number of repetition of stress till failure. Therefore, the material which has withstood the application of stress of a repetition number in excess of $10^6$ cycles will not be failed and used semi-permanentally unless the level of the stress is changed. This can be considered, from the view point of X-ray diffraction, that the change of the halfvalue width is sufficiently small. Considering that there is a distinctive fatigue limit, the precise determining of the residual life is required only after the residual life has come down below the order of $10^6$ cycles. For making the complete use of the structural member to the limit of use, it is necessary to determine the residual life down to the last one cycle. However, practically, it is considered that the judgement of residual life at an order of $10^4$ to $10^5$ cycles will be enough, taking the safety factor into account.

Therefore, in the event that the residual life after occurrence of a crack is of concern in a so-called large article, the check of the crack growth rate is commenced preferably after the moment at which the residual life is presumed to be $10^4$ to $10^5$ cycles.

Although the invention has been described on the assumption that the material of the structural member to be examined is carbon steels, the invention can be equally applied to determine the residual life of the structural member made of other materials such as stainless steel, copper, aluminum and so forth.

As has been described, according to the method of the invention, it is possible to determine the residual life of a structural member simply by a measurement of the halfvalue width in an X-ray diffraction profile. Thus, the method of the invention can be carried out easily and simply at any time as desired.

From the foregoing description, it will be seen that the invention provides a method using an X-ray to determine the residual life of a structural member in an easy and simple manner, and makes it possible to simply and easily determine the residual life of a cracked member, thus contributing greatly to bring about the industrial advantages.

What is claimed is:

1. A method for determining the residual life of a structural member composed of a metal or alloy, making use of an X-ray, comprising:
    preparing a plurality of test pieces made of the same material and subjected to the same working and heat-treating conditions as the structural member to be examined of which the fatigue strength is in question;
    executing fatigue tests with said test pieces till failure under a plurality of different stress conditions above the fatigue limit;
    obtaining for each stress condition the relationship between the residual life of said test piece and the halfvalue width ratio of the X-ray diffraction profile;
    determining, from the above-mentioned relationships, a substantially common relationship interval between the residual life and the halfvalue width ratio in the region of short residual life that is, therefore, independent of the stress conditions;
    measuring said halfvalue width ratio of said structural member; and
    determining the residual life of said structural member from the measured halfvalue width ratio in accordance with said common relationship interval.

2. A method for determining the residual life as claimed in claim 1, wherein the safety limits of said residual life are 1.07 or below and 0.96 or above in terms of the halfvalue width ratio, when said structural member is made of an annealed carbon steel and when said structural member is made of a worked carbon steel, respectively.

3. A method for determining the residual life as claimed in claim 1, wherein the measurement of the halfvalue width of said structural member is made at a portion of the latter where a concentration of stress is expected or an increase of the stress is expected.

4. A method for determining the residual life of a structural member composed of a metal or alloy, making use of an X-ray, comprising:
    preparing a plurality of test pieces made of the same material and subjected to the same working and heat-treating conditions as said structural member of which the fatigue strength is in question;

executing fatigue tests with said test pieces till failure under a plurality of different stress conditions above the fatigue limit;

obtaining for each stress condition the relationship between the residual life of said test piece and the halfvalue width ratio of the X-ray diffraction profile;

determining, from the above-mentioned relationships, a substantially common relationship interval between the residual life and the halfvalue width ratio in the region of short residual life that is, therefore, independent of the stress conditions;

determining a crack relationship between the crack length and the residual life from said halfvalue width and the crack growth rate;

determining the residual life of said structural member from the halfvalue width ratio obtained with said structural member, in accordance with said common relationship interval;

checking an occurrence of crack in said structural member when the determined residual life is short;

measuring, when any crack is found out, the length of said crack; and determining the residual life of said structural member from the measured length of said crack in accordance with said crack relationship.

5. A method for determining the residual life of a structural member composed of a metal or alloy as claimed in claim 4, wherein the check of occurrence of said crack is commenced when the residual life determined in accordance with said common relationship interval has come down below $10^4$ to $10^5$ cycles.

6. A method for determining the residual life of a structural member composed of a metal or alloy as claimed in claim 4, wherein the determination of said crack relationship is made by a process which comprises the steps of:

measuring the halfvalue widths $b_1$, $b_2$, $b_3$ ... corresponding to crack lengths $a_1$, $a_2$, $a_3$ ...;

determining the crack growth rates $da_1/dN_1$, $da_2/dN_2$, $da_3/dN_3$ ... from the halfvalue width ratios corresponding to said halfvalue widths; and drafting a coordinate system in which the axis of abscissa and axis of ordinate represent, respectively, the number N of repetition of stress and the crack length a by drawing a line of a gradient $da_1/dN_1$ from the point $Q_1$ of intersection between a line representing a crack length $a_1$ and a line representing corresponding number $N_1$ of repetition of stress when said halfvalue width $b_1$ is measured to the point 0 of origin of said coordinate, extending said line to a point $Q_1'$ where it intersects a line representing $(a_1+a_2)/2$, drawing a line of a gradient $da_2/dN_2$ from a point $Q_2$ of intersection between a line representing a crack length $a_2$ and a line representing corresponding number $N_2$ of repetition of stress when said halfvalue width $b_2$ is measured to said point $Q_1'$, extending said line of the gradient $da_2/dN_2$ to a point $Q_2'$ where it intersects a line representing $(a_2+a_3)/2$, and repeating this step to form a curve representing the crack growth rate.

* * * * *